(12) United States Patent
Nagahama

(10) Patent No.: US 8,611,638 B2
(45) Date of Patent: Dec. 17, 2013

(54) PATTERN INSPECTION METHOD AND PATTERN INSPECTION APPARATUS

(75) Inventor: Ichirota Nagahama, Koga (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 353 days.

(21) Appl. No.: 13/014,226

(22) Filed: Jan. 26, 2011

(65) Prior Publication Data

US 2012/0026316 A1 Feb. 2, 2012

(30) Foreign Application Priority Data

Jul. 27, 2010 (JP) ................................. 2010-168333

(51) Int. Cl.
*G06K 9/00* (2006.01)

(52) U.S. Cl.
USPC .......................................................... 382/145

(58) Field of Classification Search
USPC .............. 382/141–149, 218, 199; 348/86, 92, 348/125
See application file for complete search history.

(56) References Cited

U.S. PATENT DOCUMENTS

| | | | | |
|---|---|---|---|---|
| 5,995,219 A * | 11/1999 | Tabata | ...................... | 356/237.5 |
| 6,868,175 B1 | 3/2005 | Yamamoto et al. | | |
| 7,155,052 B2 * | 12/2006 | Geshel et al. | .................. | 382/144 |
| 7,551,767 B2 * | 6/2009 | Tsuchiya et al. | .............. | 382/144 |
| 8,036,446 B2 | 10/2011 | Ikenaga et al. | | |
| 8,126,259 B2 * | 2/2012 | Shimura | ....................... | 382/149 |
| 8,355,559 B2 * | 1/2013 | Harada et al. | .................. | 382/141 |
| 2003/0007677 A1 * | 1/2003 | Hiroi et al. | ..................... | 382/149 |
| 2005/0226494 A1 | 10/2005 | Yamamoto et al. | | |
| 2006/0239535 A1 * | 10/2006 | Takada et al. | ................. | 382/145 |
| 2006/0270072 A1 | 11/2006 | Ikenaga et al. | | |

FOREIGN PATENT DOCUMENTS

| | | |
|---|---|---|
| JP | 61-279128 | 12/1986 |
| JP | 2007-149055 | 6/2007 |

OTHER PUBLICATIONS

Notification of Reason for Rejection issued by the Japanese Patent Office on Sep. 13, 2013, for Japanese Patent Application No. 2010-168333, and English-language translation thereof.

* cited by examiner

*Primary Examiner* — Daniel Mariam
(74) *Attorney, Agent, or Firm* — Finnegan, Henderson, Farabow, Garrett & Dunner, L.L.P.

(57) ABSTRACT

According to an embodiment, a pattern inspection apparatus includes an imaging unit, a defect detection unit, and an inspection control unit. The imaging unit is configured to image a pattern on a substrate to acquire a pattern image. The defect detection unit is configured to detect a defect of the pattern by a first outer shape comparison in associate with the pattern image and design information for the pattern or by a comparison in pixel values between images of patterns designed to be formed into the same shape in the substrate. The inspection control unit is configured to select an inspection based on the amount of the defect detected by the first outer shape comparison or based on a value of a gradient of an edge profile of the pattern image and to control the imaging unit and the defect detection unit in accordance with the selected inspection.

6 Claims, 13 Drawing Sheets

PATTERN INSPECTION METHOD AND PATTERN INSPECTION APPARATUS

CROSS REFERENCE TO RELATED APPLICATIONS

This application is based upon and claims the benefit of priority from the prior Japanese Patent Application No. 2010-168333, filed on Jul. 27, 2010, the entire contents of which are incorporated herein by reference.

FIELD

Embodiments described herein relate generally to a pattern inspection method and a pattern inspection apparatus.

BACKGROUND

Recently, a die-to-database inspection technique has been suggested as a method of inspecting a pattern on a substrate for defects. According to this technique, an edge of a secondary electron image obtained by scanning the substrate with an electron beam is compared with an edge of a pattern of design data, and the amount of a deviance therebetween is inspected.

However, the die-to-database inspection has a problem of false defects that are frequently generated depending on the outer shape of the design pattern and a luminance change in the vicinity of an edge of a secondary electron pattern.

The problem of depending on the outer shape of the design pattern is caused when the design pattern includes a corner of a wiring line or a curve of a contact hole or the like. For example, if the die-to-database inspection is conducted on an inspection image of the wiring line including the corner, the corner is depicted in a rectangular shape on the design pattern, but the corner has a round curve shape in an actual pattern formed on the substrate. As a result, the distance of a deviance between the inspection target pattern and the design pattern is great in the corner. Thus, the corner is not actually a defect; nevertheless the corner may be detected as a defect (see reference numbers 80 and 81 in FIG. 6). If such a false defect is frequently generated, it is difficult to extract a true defect from an inspection result. This requires a considerable amount of time and effort to review and analyze the inspection result.

Furthermore, in a die-to-die inspection, a pattern edge has to be extracted from at least two or more secondary electron pattern images for comparison. However, there are pattern images having a small image value gradient (luminance change) in the vicinity of the pattern edge. It is difficult to determine an edge portion from such an image having a so-called blurred pattern edge. As a result, an error occurs in the detection of the position of the edge, leading to an increase of false defects. This is the problem of depending on the luminance change in the vicinity of the edge of the pattern image.

DETAILED DESCRIPTION

In accordance with an embodiment, a pattern inspection apparatus includes an imaging unit, a defect detection unit, and an inspection control unit. The imaging unit is configured to image a pattern on a substrate to acquire a pattern image. The defect detection unit is configured to detect a defect of the pattern by a first outer shape comparison in associate with the pattern image and design information for the pattern or by a comparison in pixel values between images of patterns designed to be formed into the same shape in the substrate. The inspection control unit is configured to select an inspection based on the amount of the defect detected by the first outer shape comparison or based on a value of a gradient of an edge profile of the pattern image and to control the imaging unit and the defect detection unit in accordance with the selected inspection.

Embodiments will now be explained with reference to the accompanying drawings.

Although a secondary electron pattern image obtained by a scanning electron microscope is described below as an example of a pattern image, the pattern image is not limited to the secondary electron pattern image. For example, a light-microscopic image can also be used. However, in the case of the inspection of, for example, a semiconductor pattern that requires a high resolution, it is preferable to use the secondary electron pattern image. A substrate includes not only a semiconductor substrate but also a ceramic substrate or glass substrate. In the accompanying drawings, like reference numbers are assigned to like parts, and such parts are repeatedly explained only when necessary.

(A) Pattern Inspection Apparatus

Figure 1:
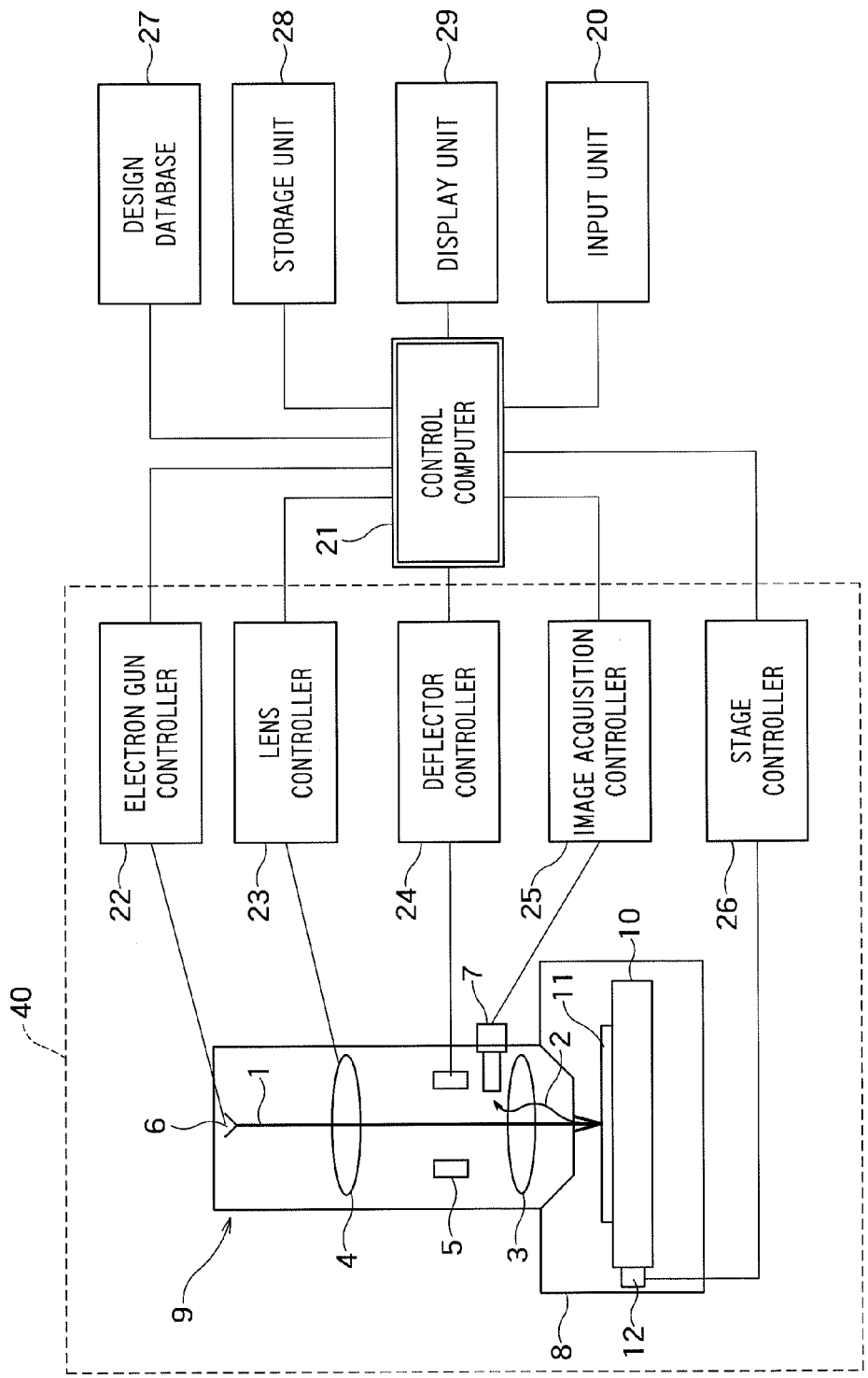
FIG. 1 is a block diagram showing a rough configuration of a pattern inspection apparatus according to one embodiment.

FIG. 1 is a block diagram showing a rough configuration of a pattern inspection apparatus according to one embodiment. The pattern inspection apparatus shown in FIG. 1 comprises a scanning electron microscope 40, a control computer 21, a design database 27, a storage unit 28, a display unit 29 and an input unit 20. The control computer 21 is connected to the design database 27, the storage unit 28, the display unit 29 and the input unit 20.

The scanning electron microscope 40 corresponds to, for example, an imaging unit in the present embodiment. The scanning electron microscope 40 comprises a column 9, a sample chamber 8, an electron gun controller 22, a lens controller 23, a deflector controller 24, an image acquisition controller 25 and a stage controller 26. The column 9 is provided with an electron gun 6, a condenser lens 4, a deflector 5, an objective lens 3 and a detector 7. A stage 10 and an actuator 12 are provided in the sample chamber 8. The stage 10 supports a substrate 11 which is a sample having an inspection target pattern formed therein.

The control computer 21 is also connected to the electron gun controller 22, the lens controller 23, the deflector controller 24, the image acquisition controller 25 and the stage controller 26. The electron gun controller 22 is connected to the electron gun 6 in the column 9. The lens controller 23 is connected to the condenser lens 4. The deflector controller 24 is connected to the deflector 5. The image acquisition controller 25 is connected to the detector 7. The stage controller 26 is connected to the actuator 12 in the sample chamber 8.

The electron gun controller 22 generates a control signal in accordance with an instruction by the control computer 21. In response to this control signal, the electron gun 6 emits an electron beam 1. The emitted electron beam 1 is focused by the condenser lens 4, and then the focal position of the electron beam 1 is adjusted by the objective lens 3 so that the electron beam 1 is applied to the substrate 11. The lens controller 23 generates a control signal in accordance with an instruction by the control computer 21. In response to this control signal, the condenser lens 4 focuses the electron beam 1. The deflector controller 24 generates a control signal in accordance with an instruction by the control computer 21. In response to the control signal sent from the deflector controller 24, the deflector 5 forms a deflected electric field or deflected magnetic field to properly deflect the electron beam 1 in an X direction and a Y direction so that the surface of the substrate 11 is scanned.

A secondary electron, a reflected electron and a back scattering electron are generated from the surface of the substrate 11 by the radiation of the electron beam 1. The electrons are detected by the detector 7, and a detection signal is sent to the control computer 21 via the image acquisition controller 25 accordingly. The control computer 21 processes the detection signal generated by the detector 7 and sent from the image acquisition controller 25, and thereby forms an image (scanning electron microscope (SEM) image) of the pattern on the surface of the sample. The control computer 21 displays the image on the display unit 29, and stores the image in the storage unit 28. The stage 10 is movable in the X direction and the Y direction. The actuator 12 moves the stage 10 in accordance with a control signal which is generated by the stage controller 26 in response to an instruction from the control computer 21. As a result, an inspection area (see the reference number 30 in FIG. 3) is scanned with the electron beam.

CAD data for the inspection target pattern is stored in the design database 27. A recipe file that describes the procedure of a later-described pattern inspection method is stored in the storage unit 28. This recipe file is read by the control computer 21 so that the pattern is inspected.

The input unit 20 is an interface for inputting the following information to the control computer 21: a coordinate position of the inspection area, the kind of inspection pattern, inspection conditions, and various thresholds for defect detection (a defect count threshold DATAHi for each divided inspection area, a defect count threshold DPTHn for each pattern kind, a pattern edge profile gradient value $\alpha$THk, an inter-edge deviance distance threshold LATHj in a die-to-database inspection, an inter-edge deviance distance threshold LBTH in a die-to-die inspection, and a pattern pixel value difference threshold CATH).

A more detailed configuration of the control computer 21 is described with reference to a rough configuration diagram of FIG. 2.

The control computer 21 comprises an inspection controller 41, an inspection setter 44, a pattern edge generator 42, an edge deviance value calculator 43, a pattern edge profile generator 50, a pattern edge profile gradient value calculator 51, a pattern pixel value difference calculator 49, a defect determiner 45, a defect count calculator 48, a defect detection technique selector 47 and an inspection result output 46.

The inspection setter 44 acquires necessary design data from the design database 27 on the basis of information such as the coordinates of the inspection area, the kind of inspection pattern and the inspection conditions that are input via the input unit 20. Out of the acquired design data, information on the edge of the design pattern is sent to the edge deviance value calculator 43.

Figure 3:
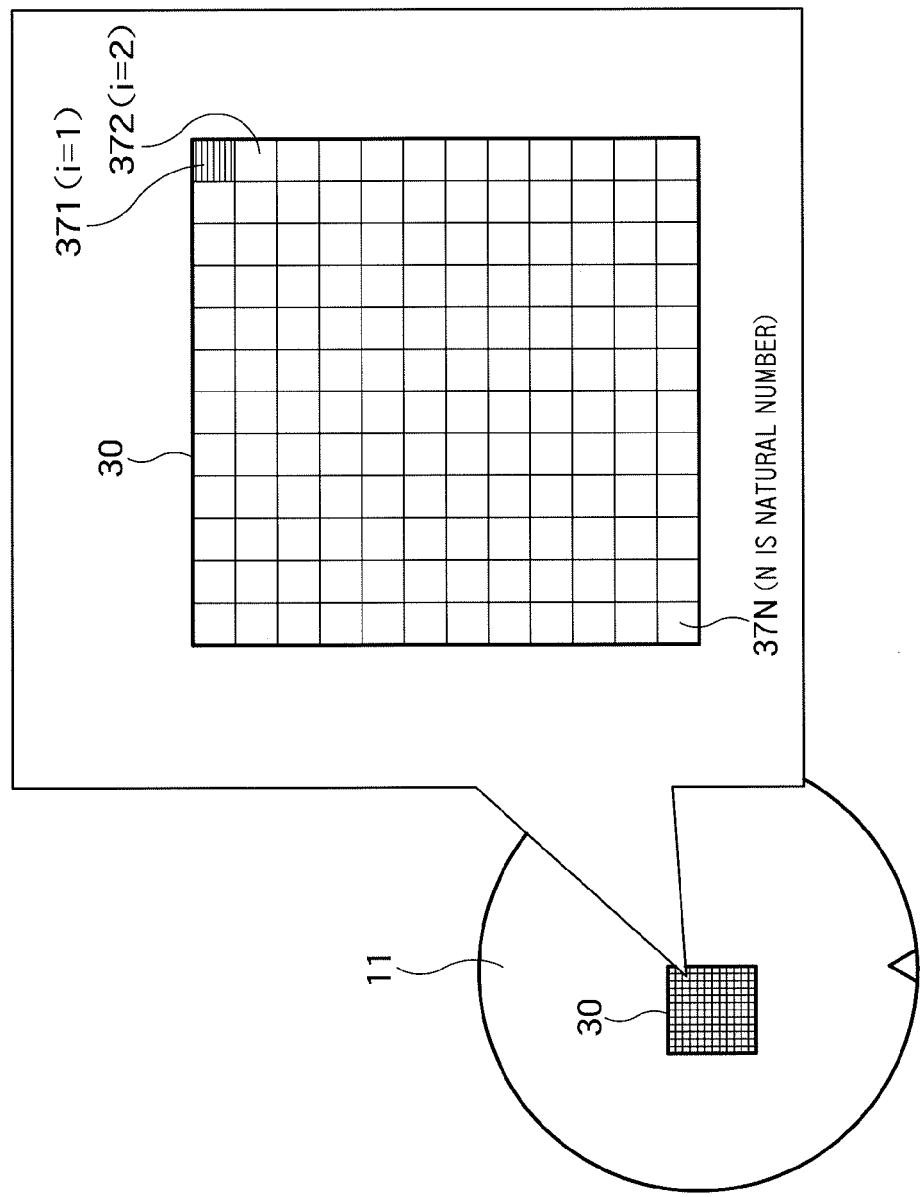
FIG. 3 is a diagram showing an example of how an inspection area is divided.

As shown in FIG. 3, the inspection setter 44 also divides the inspection area 30 in the inspection substrate 11 (for edge extraction of the design pattern) into a plurality of divided inspection areas 37$i$ ($i$=1 to N: N is a total number of divided areas). In the example shown in FIG. 3, the total number of divided areas N=$12^2$=144.

The inspection controller 41 controls the scanning electron microscope 40 to obtain an image of the pattern. The inspection controller 41 also sends an inspection result finally obtained by the later-described inspection method to the inspection result output 46.

The inspection result output 46 displays, on the display unit 29, defect information extracted by the defect determiner 45, and information on the finally obtained inspection result output by the inspection controller 41. The inspection result output 46 also stores the information in the storage unit 28.

The pattern edge generator 42 is supplied with a secondary electron pattern image from the scanning electron microscope 40, detects an edge of the pattern from the pattern image, and sends, to the edge deviance value calculator 43, information on the pattern edge which is a detection result.

The edge deviance value calculator 43 matches the edge of the inspection pattern to an edge of another pattern, calculates a deviance distance LA between these edges, and sends the deviance distance LA to the defect determiner 45. Here, as described in detail later, the edge of another pattern is equivalent to the edge of the design pattern that corresponds to the inspection pattern in the die-to-database inspection. In the die-to-die inspection, the edge of another pattern is equivalent to an edge of a different pattern (hereinafter referred to as a "reference pattern") which is formed in the divided inspection area different from the divided inspection area where the inspection pattern is formed within the inspection area and which is designed to have the same shape as the inspection pattern.

The pattern pixel value difference calculator 49 is supplied with an inspection pattern image and a reference pattern image from the scanning electron microscope 40. The pattern pixel value difference calculator 49 superposes pixels of the inspection pattern image on pixels of the reference pattern image. Thus, the pattern pixel value difference calculator 49 calculates a difference CA between a pixel value of the inspection pattern and a pixel value of the reference pattern, and sends the calculation result to the defect determiner 45 and the defect detection technique selector 47.

The defect determiner 45 extracts defects by comparing the calculation result with the various thresholds, and sends information on the defects to the inspection result output 46 and the defect count calculator 48.

From the information of the defects extracted by the defect determiner 45 and sent from the defect determiner 45, the defect count calculator 48 calculates a total number of defects DATHi in the divided inspection area 37$i$, or calculates a total number of defects DPn for each kind n of inspection pattern in the divided inspection area 37i, and sends a calculation result to the defect detection technique selector 47.

The pattern edge profile generator 50 is supplied with a secondary electron pattern image from the scanning electron microscope 40, and acquires a profile of the edge of the inspection pattern from the inspection pattern image and then sends the profile to the pattern edge profile gradient value calculator 51.

The pattern edge profile gradient value calculator 51 calculates a value $\alpha k$ (k=1 to R: R is the total number of pattern edges) of the gradient of the edge of the inspection pattern from the profile sent from the pattern edge profile generator 50, and sends the value $\alpha k$ to the defect detection technique selector 47.

The defect detection technique selector 47 compares the amount of defects detected by the die-to-database inspection or the value of the gradient of the edge profile of the inspection pattern with each threshold. The defect detection technique selector 47 thus selects an inspection method on the basis of the comparison result. It should be noted that the threshold of the amount of defects is set for each divided inspection area or for each kind of inspection pattern.

In the present embodiment, the inspection controller 41, the defect count calculator 48, the pattern edge profile generator 50, the pattern edge profile gradient value calculator 51 and the defect detection technique selector 47 correspond to, for example, an inspection control unit.

In the present embodiment, the pattern edge generator 42, the edge deviance value calculator 43, the pattern pixel value difference calculator 49 and the defect determiner 45 correspond to, for example, a defect detection unit.

Now, the pattern inspection method that uses the pattern inspection apparatus shown in FIG. 1 is described with reference to FIG. 4 to FIG. 11.

(B) Pattern Inspection Method (1) First Embodiment

Figure 4:
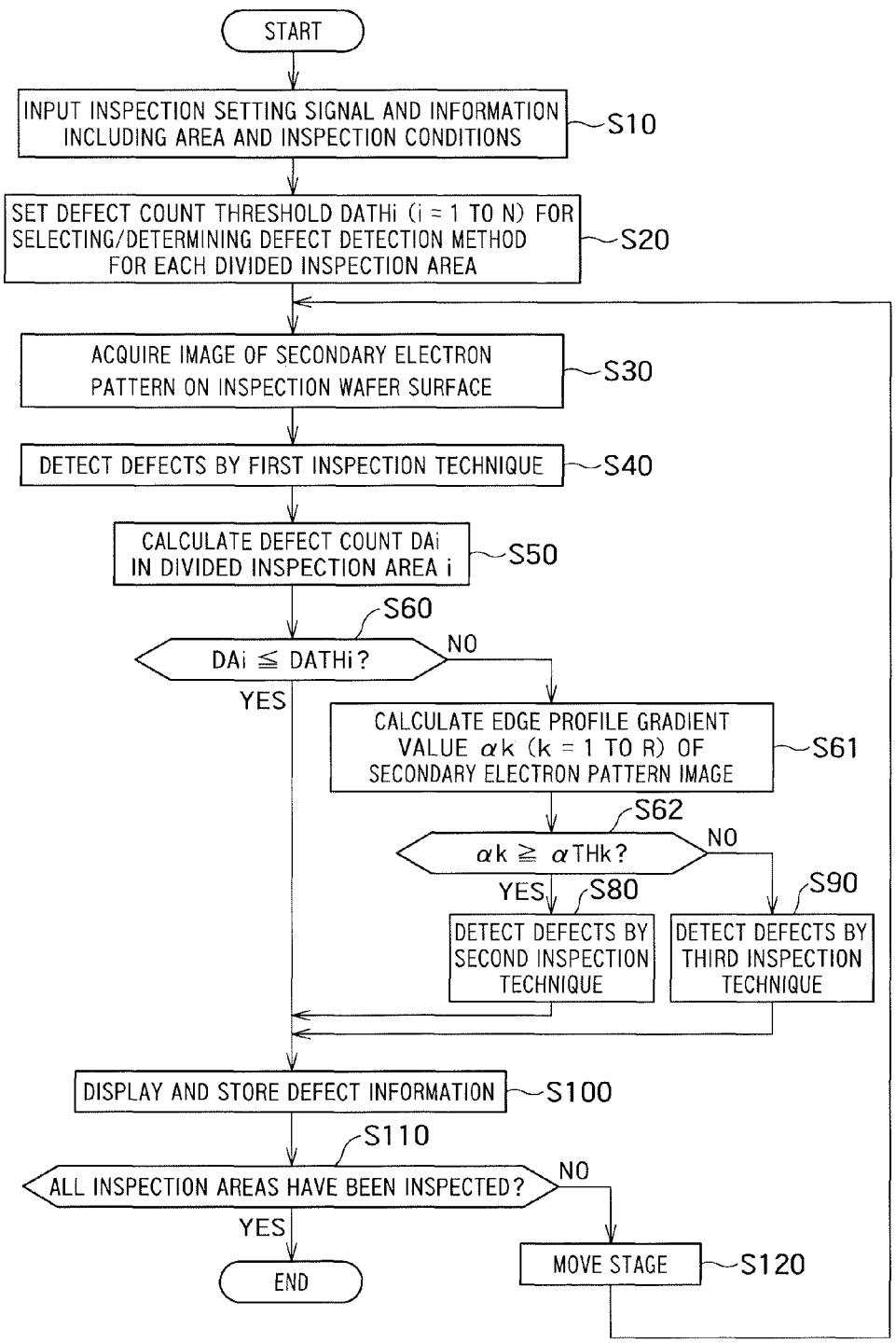
FIG. 4 is a flowchart showing a rough process of a pattern inspection method according to a first embodiment.

FIG. 4 is a flowchart showing a rough process of a pattern inspection method according to the present embodiment.

First, an inspection setting signal in input to the inspection setter 44 from the input unit 20. In response to the input of the inspection setting signal, the inspection setter 44 retrieves necessary design information from the design database 27. Further, information such as the inspection area coordinates and the inspection conditions are input to the inspection setter 44 from the input unit 20 by reference to the design information (step S10). The inspection conditions include the defect count threshold DATHi for divided inspection area i and the pattern edge profile gradient threshold $\alpha$THk. The inspection setter 44 sends the defect count threshold DATHi to the defect detection technique selector 47, and sends the pattern edge profile gradient threshold $\alpha$THk to the pattern edge profile gradient value calculator 51. In the present embodiment, the defect count threshold DATHi and the pattern edge profile gradient threshold $\alpha$THk correspond to, for example, first and second thresholds, respectively.

Furthermore, the defect count threshold DATHi for selecting/determining a defect extraction method for each divided inspection area 37i is input to the inspection setter 44 from the input unit 20 (step S20). Information on the input defect count threshold DATHi is sent to the defect count calculator 48 from the inspection setter 44.

Furthermore, the inspection controller 41 generates a control signal and sends the control signal to the scanning electron microscope 40 so that a secondary electron pattern image of the inspection pattern within the divided inspection area 37i is acquired (step S30). The acquired secondary electron pattern image is sent to the pattern edge generator 42 and the pattern edge profile generator 50.

Furthermore, the defect detection technique selector 47 selects a first inspection technique based on the die-to-database inspection, and defects are detected by the pattern edge generator 42, the edge deviance value calculator 43 and the defect determiner 45 (step S40). The defect determiner 45 sends the detection result to the defect count calculator 48. In the present embodiment, the first inspection technique corresponds to, for example, a defect detection technique based on a first outer shape comparison.

Moreover, the defect count calculator 48 calculates a defect count DAi in the divided inspection area 37i, and sends the calculation result to the defect detection technique selector 47 (step S50).

Furthermore, the defect detection technique selector 47 compares the calculated defect count DAi with the defect count threshold DATHi (step S60). When the comparison result shows that the defect count DAi the defect count threshold DATHi, the defect detection technique selector 47 determines that the number of false defects is small. Thus, the detection result by the first inspection technique is displayed on the display unit 29 via the inspection result output 46 as final defect information, and stored in the storage unit 28 (step S100). On the other hand, when the comparison result shows that the defect count DAi>the defect count threshold DATHi, defect detection is again carried out by a second inspection technique or a third inspection technique (step S61 to S90). Further details of the repeated defect detection are as follows.

Specifically, the pattern edge profile generator 50 generates a pattern edge profile from the acquired secondary electron pattern image, and sends the pattern edge profile to the edge profile gradient value calculator 51. The pattern edge profile gradient value calculator 51 calculates a pattern edge profile gradient value $\alpha k$ from the sent pattern edge profile (step S61), compares the pattern edge profile gradient value $\alpha k$ with the pattern edge profile gradient threshold $\alpha$THk (step S62), and sends a comparison result to the defect detection technique selector 47.

When the pattern edge profile gradient value $\alpha k \geq$ the pattern edge profile gradient threshold $\alpha$THk, the defect detection technique selector 47 determines that there is a sufficient luminance change in the vicinity of the edge of the secondary electron pattern image, and selects the second inspection technique based on the die-to-die inspection. Further, the inspection controller 41, the scanning electron microscope 40, the pattern edge generator 42, the edge deviance value calculator 43 and the defect determiner 45 again conduct defect detection (step S80). The inspection result output 46 displays the result of the redetection on the display unit 29 as final defect information, and stores the result in the storage unit 28 (step S100). In the present embodiment, the second inspection technique corresponds to, for example, a defect detection technique based on a second outer shape comparison.

When the pattern edge profile gradient value $\alpha k <$ the pattern edge profile gradient threshold $\alpha$THk, the defect detection technique selector 47 determines that there is no sufficient luminance change in the vicinity of the edge of the secondary electron pattern image, and selects the third inspection technique based on pixel value comparison (step S90). Further, the pattern pixel value difference calculator 49 and the defect determiner 45 again conduct a defect detection, and the inspection result output 46 displays the result of the redetection on the display unit 29 as final defect information, and stores the result in the storage unit 28 (step S100). In the present embodiment, the third inspection technique corresponds to, for example, a defect detection technique based on a pixel value comparison between a plurality of pattern images.

If there is any uninspected divided inspection area 37*i* (step S110), the inspection controller 41 moves the stage 10 (i=i+1; step S120), and repeats the above-described procedure until defect detections for all of the inspection areas are finished.

The first to third inspection techniques described above are explained in more detail with reference to FIG. 5 to FIG. 12.

Figure 5:
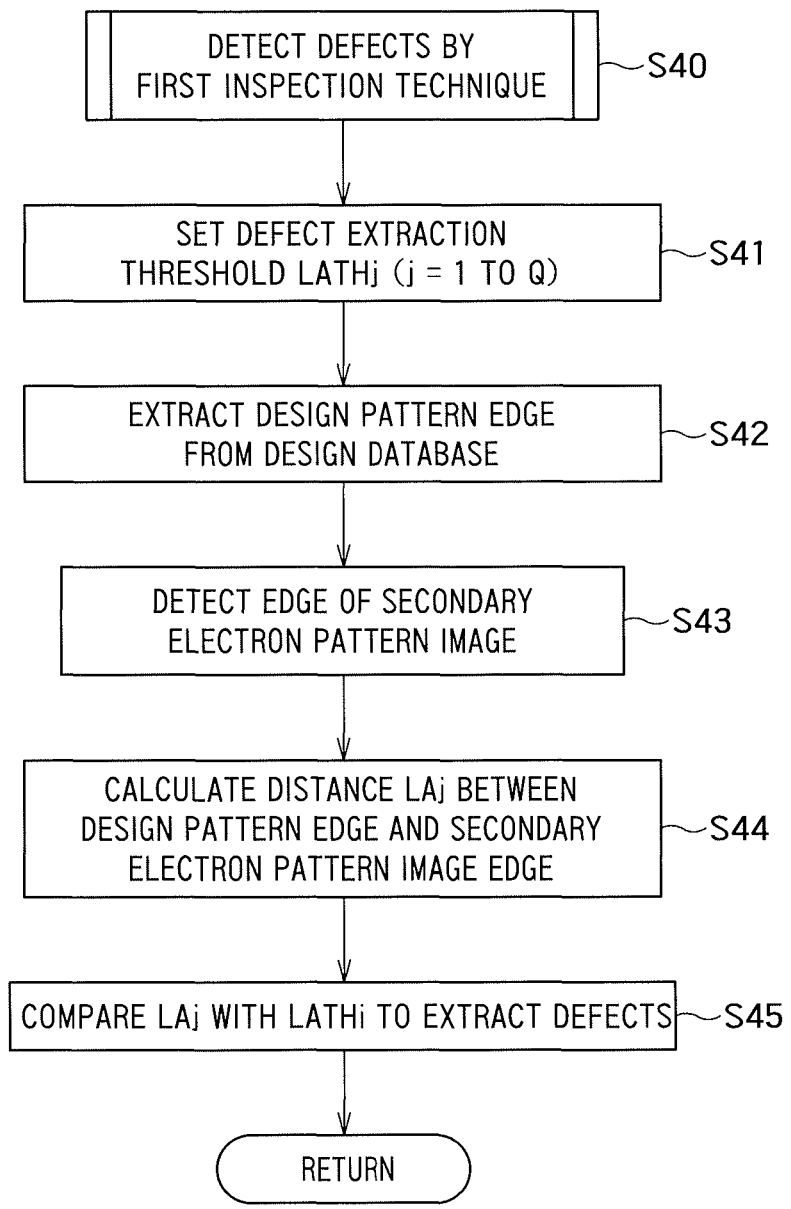
FIG. 5 is a flowchart showing a detailed process of a first inspection technique.

As shown in FIG. 5, in using the first inspection technique, the defect extraction threshold LATHj (j=1 to Q: Q is the total number of pattern kinds) is first input to the inspection setter 44 by the input unit 20 (step S41). The defect extraction threshold LATHj is set for each kind of pattern. The inspection setter 44 sends the input defect extraction threshold LATHj to the defect determiner 45.

The inspection setter 44 then retrieves edge information for a design pattern that corresponds to the inspection pattern from the design database 27 (step S42), and sends the edge information to the edge deviance value calculator 43.

Moreover, the pattern edge generator 42 detects an edge of the secondary electron pattern image (step S43), and sends the detection result to the edge deviance value calculator 43.

Furthermore, the edge deviance value calculator 43 matches the edge of the design pattern to the edge of the secondary electron pattern image, and then calculates an inter-edge distance LAj (step S44) and sends the calculation result to the defect determiner 45.

Finally, the defect determiner 45 extracts defects by comparing the sent inter-edge distance LAj with the defect extraction threshold LATHj (step S45).

Figure 6:
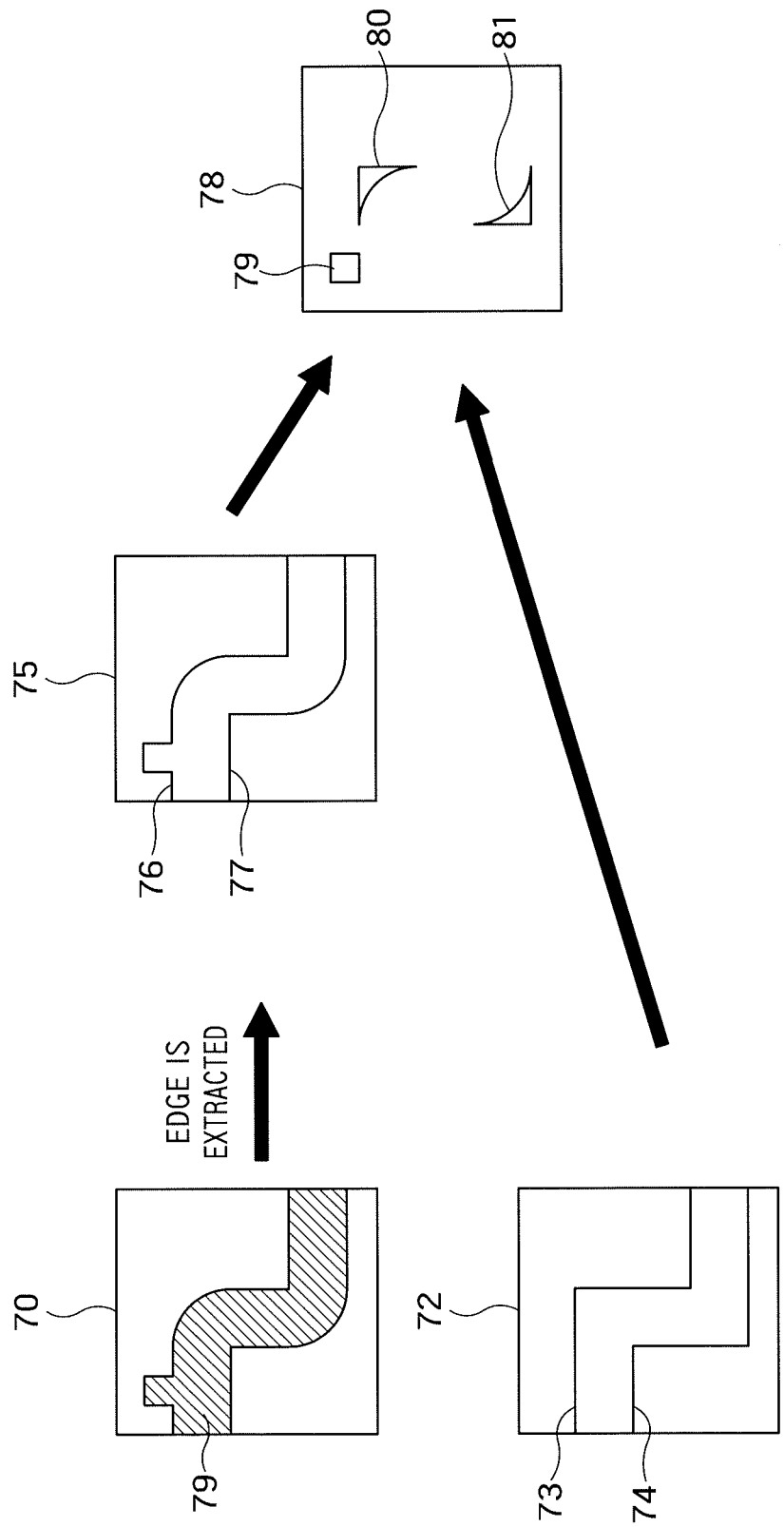
FIG. 6 is an explanatory diagram of the first inspection technique.

FIG. 6 is an explanatory diagram of the first inspection technique. Here, a design pattern that includes a cranked portion having two corners is shown as an example.

The pattern edge generator 42 detects an edge of a secondary electron pattern image 70 of an inspection pattern 71, such that an inspection pattern edge extraction image 75 in which two edges 76 and 77 are extracted is obtained. On the other hand, pattern edges 73 and 74 of a design pattern corresponding to the inspection pattern 71 have already been extracted from the design database 27 and sent to the edge deviance value calculator 43 by the inspection setter 44.

The edge deviance value calculator 43 matches a design data image 72 including the pattern edges 73 and 74 to inspection pattern edge extraction image 75, and calculates the inter-edge distance La and sends the inter-edge distance La to the defect determiner 45. Further, portions 79 to 81 having the inter-edge distance La that surpasses the defect extraction threshold LATHj are extracted as defect portions by the defect determiner 45, and displayed on the display unit 29 as an edge deviance value image 78 and stored in the storage unit 28.

In the present embodiment, the secondary electron pattern image 70 corresponds to, for example, a first pattern image, and the pattern edges 73 and 74 of the design pattern correspond to, for example, design information for a first pattern.

Now, an inspection technique selecting method (steps S61 and S62) when the defect count DAi>the defect count threshold DATHi in step S60 of FIG. 4 is described in more detail with reference to FIG. 7.

Figure 7:
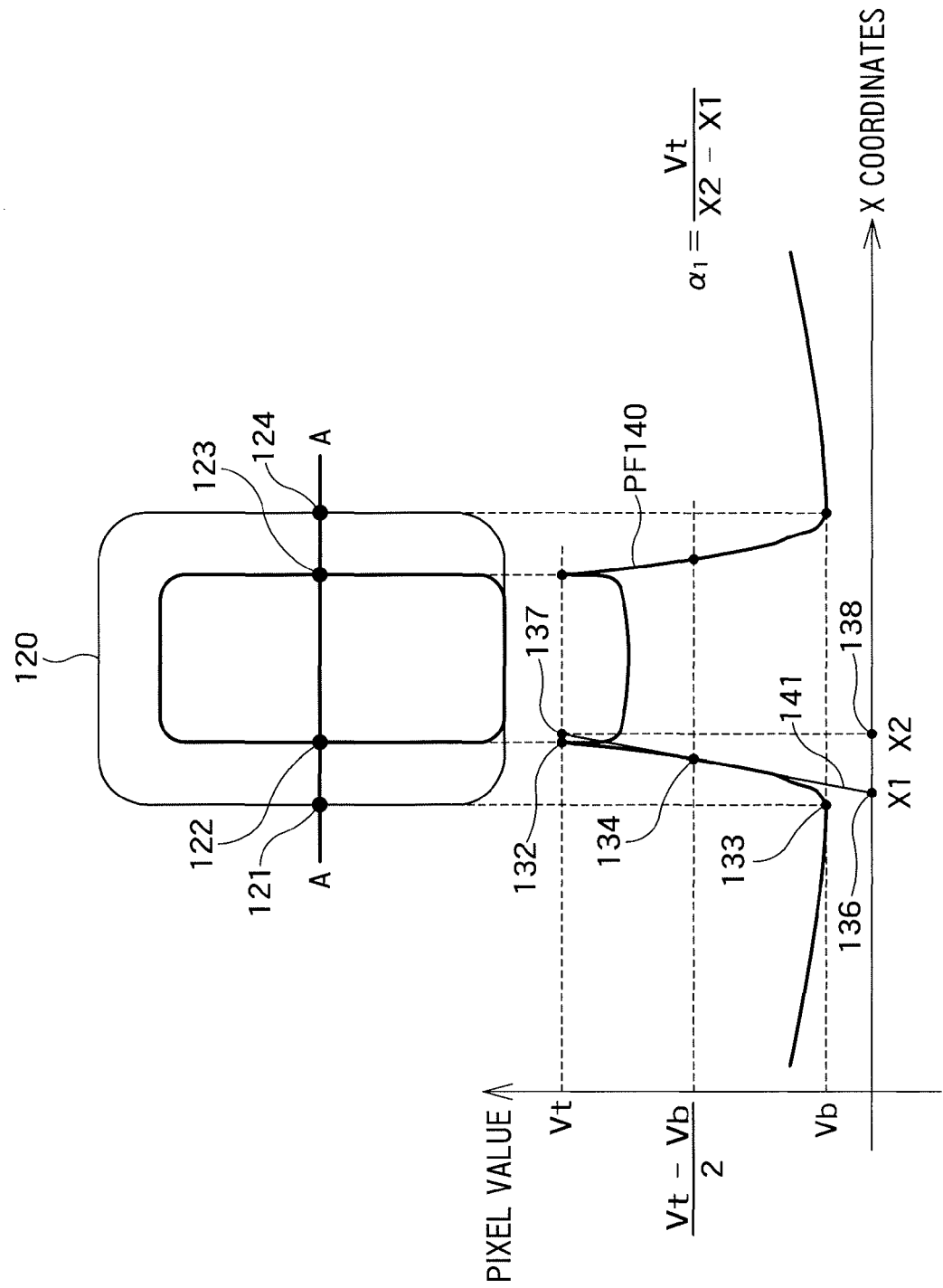
FIG. 7 is a graph illustrating an example of a method of calculating a pattern edge profile gradient value.

FIG. 7 shows a pattern image 120 which is an example of the secondary electron pattern image acquired by the scanning electron microscope 40, together with a pattern edge profile PF140 through the A-A sectional line of the pattern image 120 generated by the pattern edge profile generator 50.

Out of a rising edge and a falling edge in the pattern edge profile PF140, the edge profile gradient value calculator 51 selects, for example, the rising edge in the left of FIG. 7, and detects a point 133 and a point 132 that provide a minimum value Vb and a maximum value Vt of the pixel of the rising edge, respectively. The pattern edge profile gradient value calculator 51 then finds a tangent 141 to the pattern edge profile PF140 at a position 134 corresponding to a middle point (Vt−Vb)/2 between the minimum value Vb and the maximum value Vt of the pixel.

If Vt is divided by the difference between X coordinates X2 of a point 137 at which the tangent 141 intersects with the pixel value=Vt and X coordinates X1 of a point 136 at which the tangent 141 intersects with X coordinates (pixel value=0), an inclination $\alpha 1=Vt/(X2-X1)$ (here, k=1) of the tangent 141 is obtained. The pattern edge profile gradient value calculator 51 defines the value of $\alpha 1$ as a pattern edge profile gradient value, and sends this value to the defect detection technique selector 47 (step S61). The defect detection technique selector 47 compares the sent pattern edge profile gradient value $\alpha 1$ with a pattern edge profile gradient threshold $\alpha TH1$ (k=1) (FIG. 4, step S62).

When the comparison result shows that the pattern edge profile gradient value $\alpha 1 \geq$ the pattern edge profile gradient threshold $\alpha TH1$, the defect detection technique selector 47 determines that secondary electron pattern image 120 has a sufficient luminance change in the vicinity of its edge. The defect detection technique selector 47 thus selects a second detection technique based on the die-to-die inspection as a redetection technique.

On the other hand, when the comparison result shows that the pattern edge profile gradient value $\alpha 1 <$ the pattern edge profile gradient threshold $\alpha TH1$, the defect detection technique selector 47 determines that the secondary electron pattern image 120 does not have a sufficient luminance change in the vicinity of its edge. The defect detection technique selector 47 thus selects a third detection technique based on the pixel value comparison as a redetection technique.

Figure 8:
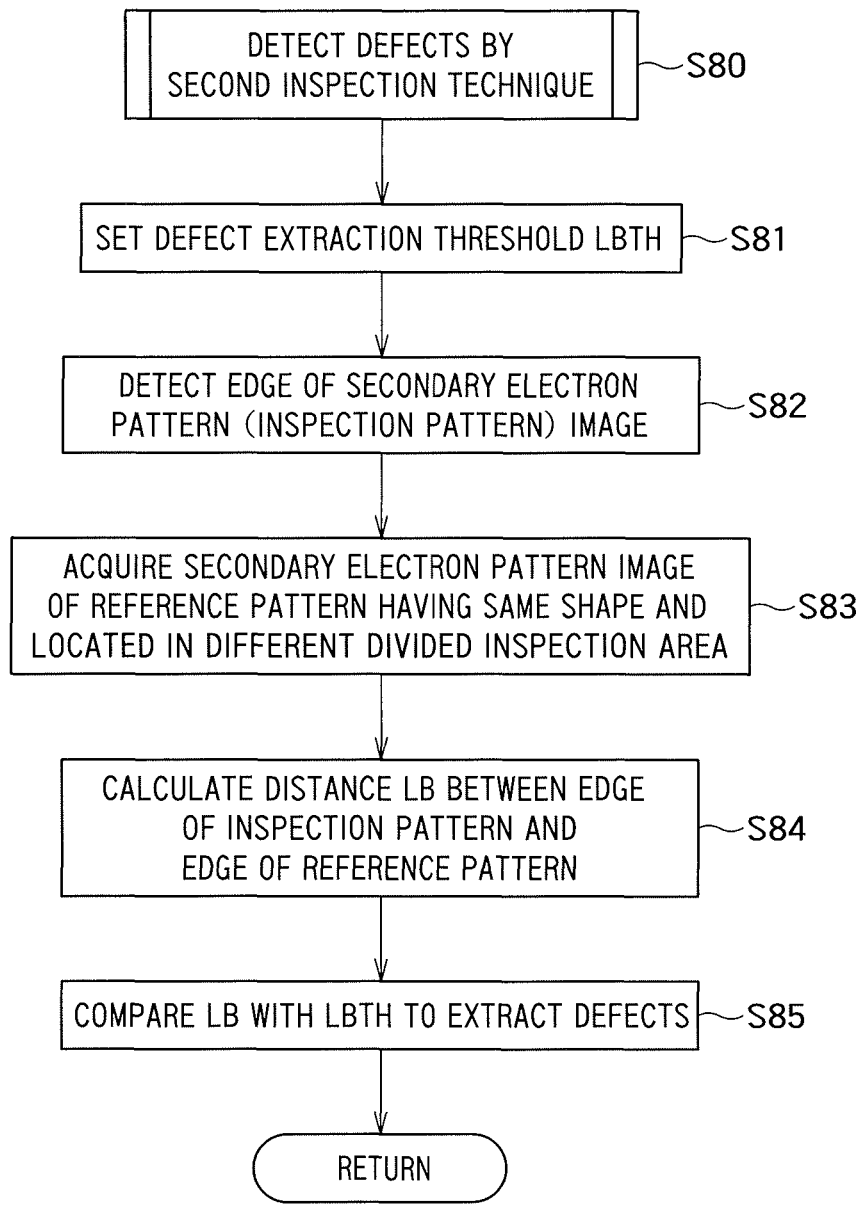
FIG. 8 is a flowchart showing a rough process of defect detection according to a second inspection technique.

Now, defect detection by the second inspection technique is described with reference to a flowchart of FIG. 8.

First, in using the second inspection technique, the defect extraction threshold LBTH is input to the inspection setter 44 by the input unit 20 (step S81). The inspection setter 44 sends the input defect extraction threshold LBTH to the defect determiner 45.

The pattern edge generator 42 then detects an edge of the secondary electron pattern image acquired from the inspection pattern, and sends the detection result to the edge deviance value calculator 43 (step S82).

Furthermore, the inspection controller causes the scanning electron microscope 40 to acquire a secondary electron pattern image of the reference pattern. The acquired image of the reference pattern is sent to the pattern edge generator 42, and an edge of a reference pattern image is also detected. The detected edge of the reference pattern is sent to the edge deviance value calculator 43.

Furthermore, the edge deviance value calculator 43 matches the edge of the inspection target pattern to the edge of the reference pattern to calculate a distance LB between these edges, and sends the calculation result to the defect determiner 45 (step S84).

Finally, the defect determiner 45 extracts defects by comparing the sent inter-edge distance LB with the defect extraction threshold LBTH (step S85).

Figure 9:
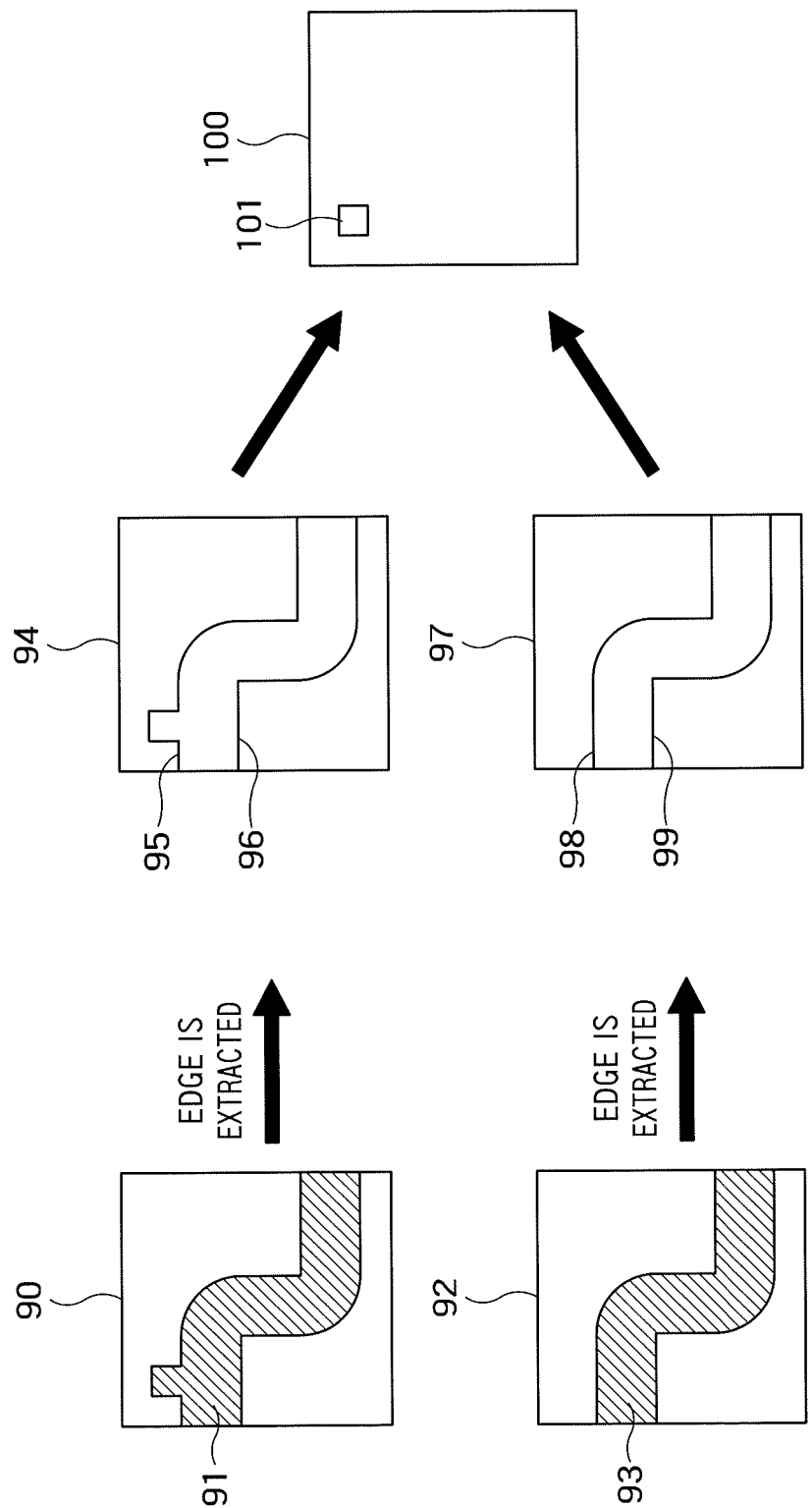
FIG. 9 is an explanatory diagram of the second inspection technique.

FIG. 9 is an explanatory diagram of the second inspection technique. Here again, a design pattern that includes a cranked portion having two corners is shown as an example.

A secondary electron pattern image 90 shown in FIG. 9 is an image of an inspection pattern 91 obtained by imaging, for example, the divided inspection area 371 (i=1). The pattern edge generator 42 detects edges of the secondary electron pattern image 90, such that an inspection pattern edge extraction image 94 in which two edges 95 and 96 are extracted is obtained. In the present embodiment, the secondary electron pattern image 90 corresponds to, for example, the first pattern image, and the divided inspection area 371 corresponds to, for example, a first area.

Similarly, a secondary electron pattern image 92 shown in FIG. 9 is, for example, an image obtained by imaging a reference pattern 93. The reference pattern 93 is formed in the divided inspection area 372 (i=2) adjacent to the divided inspection area 371, and is deigned to have the same outer shape as the inspection pattern 91. The pattern edge generator 42 also detects edges of the secondary electron pattern image 92 of the reference pattern 93, such that two edges 98 and 99 are extracted. In the present embodiment, the secondary electron pattern image 92 corresponds to, for example, a second pattern image, and the divided inspection area 372 corresponds to, for example, a second area.

The edge deviance value calculator 43 matches the inspection pattern edge extraction image 94 including the pattern edges 95 and 96 to an inspection pattern edge extraction image 97 including the pattern edges 98 and 98, so that the inter-edge distance LB is calculated. A portion 101 having the inter-edge distance LB that surpasses the defect extraction threshold LBTH is extracted as a defect portion, and displayed on the display unit 29 as an edge deviance value image 100.

Although the die-to-die inspection based on the comparison between two pattern images 91 and 93 has been shown in the present embodiment, there is no limitation to this inspection. Inspection accuracy may be enhanced by comparing three or more pattern images in accordance with required specifications.

Figure 10:
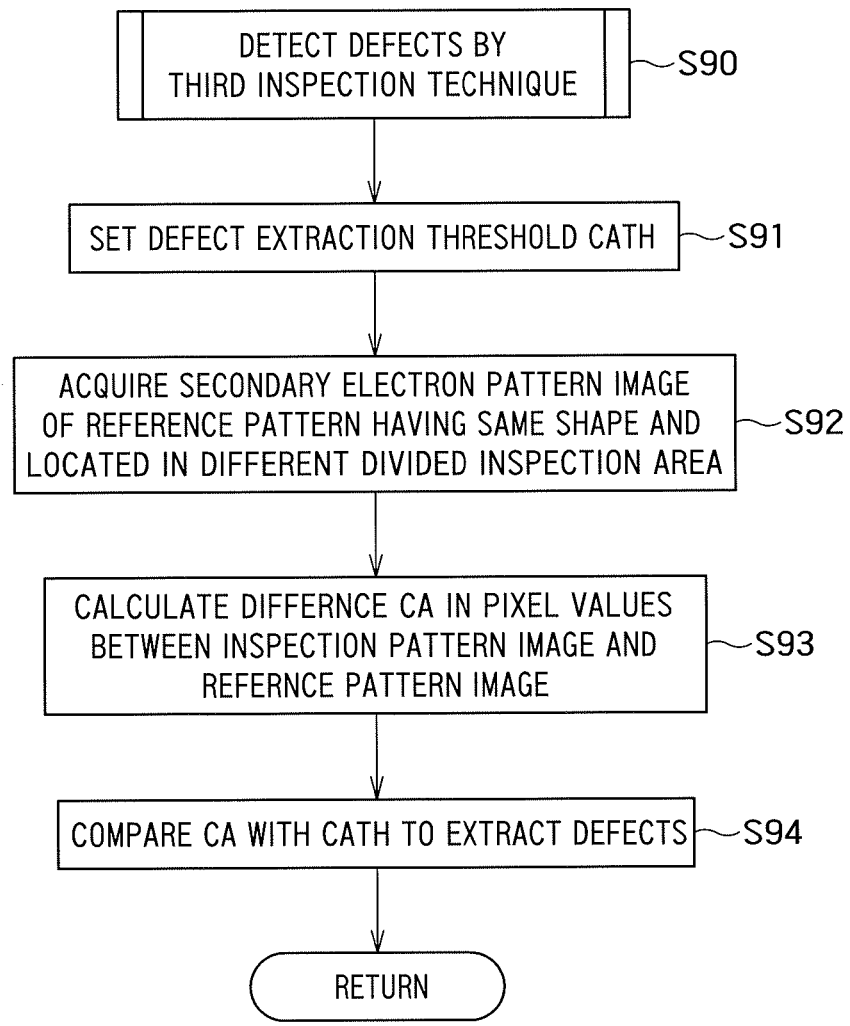
FIG. 10 is a flowchart showing a rough process of defect detection according to a third inspection technique.

Now, defect detection by the third inspection technique is described with reference to a flowchart of FIG. 10.

First, in using the third inspection technique, the defect extraction threshold CATH is input to the inspection setter 44 by the input unit 20 (step S91). The inspection setter 44 sends the input defect extraction threshold CATH to the defect determiner 45.

Furthermore, the inspection controller causes the scanning electron microscope 40 to acquire a secondary electron pattern image of the reference pattern (step S92). The acquired image of the reference pattern is sent to the pattern pixel value difference calculator 49 together with the already acquired image of the inspection pattern.

Furthermore, the pattern pixel value difference calculator 49 matches the image of the inspection pattern to the image of the reference pattern to calculate a difference CA in pixel values between these edges, and sends the calculation result to the defect determiner 45 (step S93).

Finally, the defect determiner 45 extracts defects by comparing the sent difference CA of the pixel values with the defect extraction threshold CATH (step S94).

Figure 11:
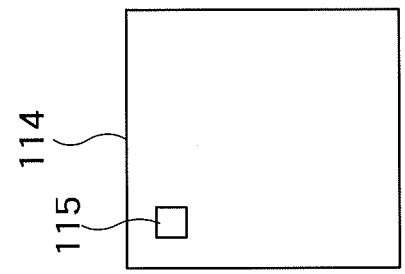
FIG. 11 is an explanatory diagram of the third inspection technique.
Figure 11:
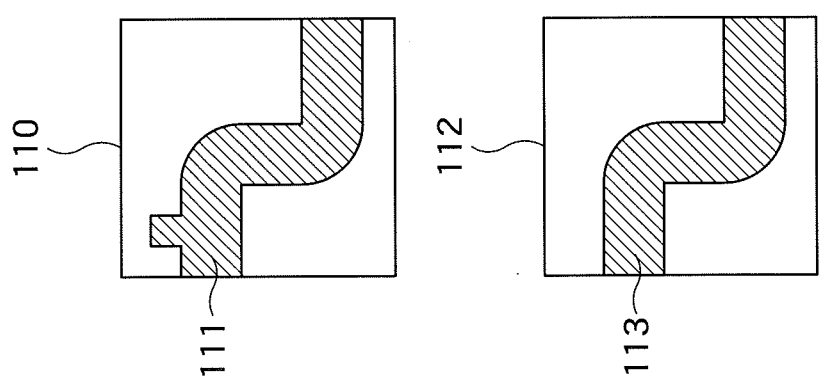

FIG. 11 is an explanatory diagram of the third inspection technique. Here again, a design pattern that includes a cranked portion having two corners is shown as an example.

The pattern pixel value difference calculator 49 matches a secondary electron pattern image 110 of an inspection pattern 111 to a secondary electron pattern image 112 of a reference pattern 113. A pixel value difference is then calculated between these images. A portion 115 that surpasses the defect extraction threshold CATH is extracted as a defect portion, and displayed on the display unit 29 as a pixel value difference image 114.

In the present embodiment, the secondary electron pattern image 110 corresponds to, for example, the first pattern image, and the secondary electron pattern image 112 corresponds to, for example, the second pattern image.

The edge shape of the design pattern is different from the edge shape of the actual pattern, for example, as in the defects 80 and 81 shown in FIG. 6. However, according to conventional inspection methods, portions which have no problem from the perspective of product specifications are also extracted as defects, and such false defects have to be removed from an inspection result. Thus, a considerable amount of time and effort are required for a defect inspection.

In contrast, according to the present embodiment, the amount of defects extracted by the die-to-database inspection is compared with a prepared first threshold. When the amount of defects is more than the first threshold, defects are redetected by the die-to-die inspection or by the inspection based on the pixel value comparison. Therefore, the amount of false defects is reduced, a load on the inspection apparatus is reduced, and the throughput of an inspection is improved.

Moreover, according to the present embodiment, in the redetection of defects, a gradient value of an edge profile in a pattern edge of an inspection pattern image is calculated and compared with the second threshold to check the degree of the gradient of the edge profile. Depending on whether the gradient is steep or gentle, one of the second inspection method and the third inspection method is selected. This enables accurate defect detection suitable to the quality of the acquired pattern image. Thus, the problem of the conventional inspection methods of the increased false defects resulting from an error in edge position detection is solved.

(2) Second Embodiment

Figure 12:
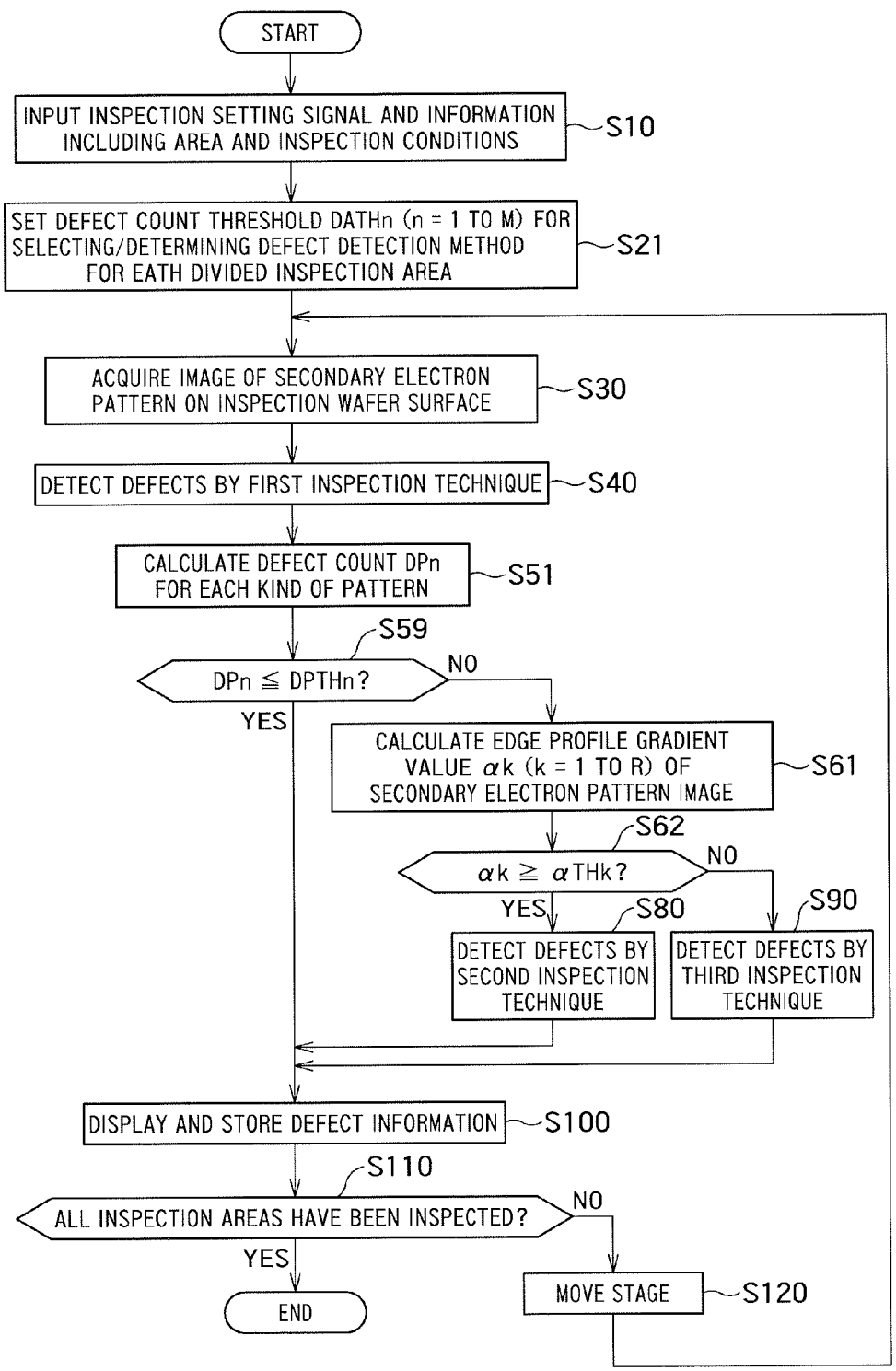
FIG. 12 is a flowchart showing a rough process of a pattern inspection method according to a second embodiment.

FIG. 12 is a flowchart showing a rough process of a pattern inspection method according to a second embodiment. As apparent from contrast with FIG. 4, the present embodiment is characterized by the process in steps S21, S51 and S59. The number of defects in the divided inspection area is brought into question in the first embodiment described above. In the present embodiment, the number of defects in an inspection area is brought into question for each kind of pattern.

Accordingly, a defect count DPn (n=1 to M: M is a total number of pattern kinds) is calculated for each kind of pattern (step S51). A defect count threshold DPTHn which serves as a standard for judging whether to perform redetection depending on the number of false defects is also set for each kind of pattern (step S21). The defect count threshold DPTHn is compared with the defect count DPn for each kind of pattern (step S59). In the present embodiment, the defect count threshold DPTHn corresponds to, for example, the first threshold.

The detailed process in the pattern inspection method according to the present embodiment is substantially the same as that according to the first embodiment shown in FIG. 4 in other respects.

(3) Third Embodiment

Figure 13:
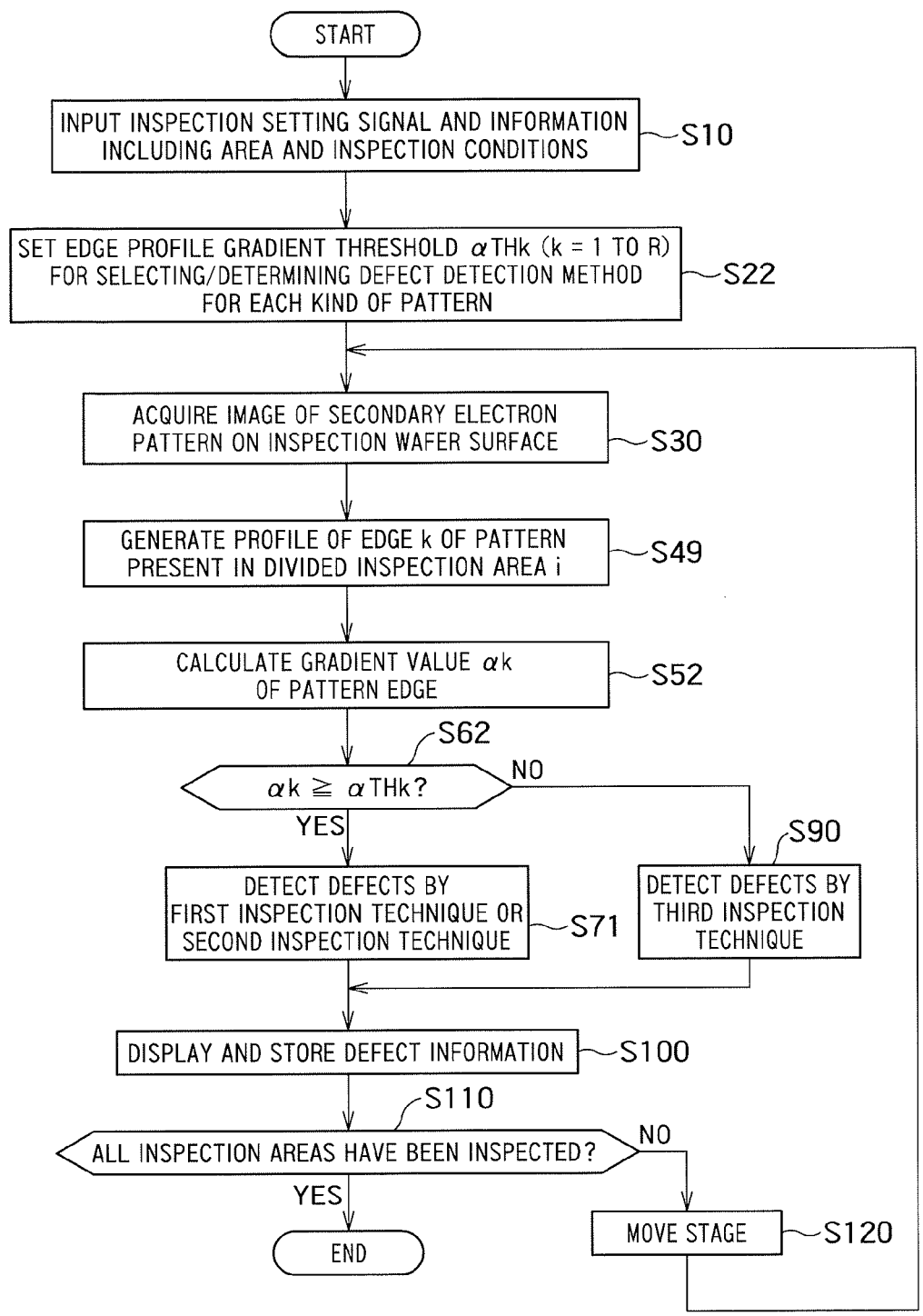
FIG. 13 is a flowchart showing a rough process of a pattern inspection method according to a third embodiment.

FIG. 13 is a flowchart showing a rough process of a pattern inspection method according to a third embodiment.

As apparent from contrast with FIG. 4 and FIG. 12, the present embodiment is characterized by the following point: Before a pattern inspection, a gradient value αk of an edge profile in a pattern edge of an inspection pattern image is calculated and compared with a gradient threshold αthk to check the degree of the gradient of the edge profile of the inspection pattern. Depending on whether the gradient is steep or gentle, one of the first and second inspection techniques based on the outer shape comparison or the third inspection technique based on the pixel value comparison is selected. The rough process is described below with reference to FIG. 13.

First, as in the first and second embodiments described above, an inspection setting signal in input to the inspection setter 44 from the input unit 20. In response to the input of the inspection setting signal, the inspection setter 44 retrieves necessary design information from the design database 27. Further, information such as the inspection area coordinates and the inspection conditions are input to the inspection setter 44 from the input unit 20 by reference to the design information (step S10).

The inspection conditions here include the defect count threshold DATHi for each divided inspection area and the edge profile gradient threshold αTHk for each pattern edge k (k=1 to R: R is a total number of pattern edges). These values are set for each kind of pattern. The inspection setter 44 sets the pattern edge profile gradient threshold αTHk and the defect count threshold DATHi, and sends these thresholds to the defect detection technique selector 47 (step S22). In the present embodiment, the pattern edge profile gradient threshold αTHk corresponds to, for example, the first threshold.

Furthermore, the inspection controller 41 generates a control signal and sends the control signal to the scanning electron microscope 40 so that a secondary electron pattern image of the inspection pattern within the divided inspection area 37i is acquired (step S30). The acquired secondary electron pattern image is sent to the pattern edge generator 42 and the pattern edge profile generator 50.

Furthermore, the pattern edge profile generator 50 generates an edge profile of the edge k of the inspection pattern in the divided inspection area 37i from the acquired secondary electron pattern image, and sends the edge profile to the pattern edge profile gradient value calculator 51 (step S49). The edge profile gradient value calculator 51 calculates a profile gradient value αk from the sent edge profile, and sends the profile gradient value αk to the defect detection technique selector 47 (step S52). The same method as that in the first embodiment described with reference to FIG. 7 can be used as a specific method of calculating the profile gradient value αk.

Furthermore, the defect detection technique selector 47 compares the pattern edge profile gradient value αk of the pattern edge k with the pattern edge profile gradient threshold αTHk (step S62).

When the comparison result shows that the pattern edge profile gradient value αk≥the pattern edge profile gradient threshold αTHk, the defect detection technique selector 47 determines that secondary electron pattern image 120 has a sufficient luminance change in the vicinity of its edge. The defect detection technique selector 47 thus selects the first inspection technique based on the die-to-database inspection or the second inspection technique based on the die-to-die inspection. In an inspection apparatus that uses a design database as the pattern inspection apparatus shown in FIG. 1 and FIG. 2, the first inspection technique is generally employed first because of its high processing speed and low load on the apparatus. When it is determined that there are more false defects, the second inspection technique is used to carry out a reinspection. In order to judge whether there are a great number or small number of false defects, the method of comparing the count DAi of defects extracted in the divided inspection area 37i with the defect count threshold DATHi can be used, as in the process described in the first embodiment (see steps S50 and S60 in FIG. 4).

Back to step S62 in FIG. 13, when the comparison result shows that the pattern edge profile gradient value α1<the pattern edge profile gradient threshold αTH1, the defect detection technique selector 47 determines that the secondary electron pattern image 120 does not have a sufficient luminance change in the vicinity of its edge. The defect detection technique selector 47 thus selects the third detection technique based on the pixel value comparison as a defect detection method (step S90).

Subsequently, the inspection result output 46 displays the detection results obtained by the selected first to third detection methods on the display unit 29 as defect information, and stores the results in the storage unit 28 (step S100).

If there is any uninspected divided inspection area (step S110), the inspection controller 41 moves the stage 10 (step S120), and repeats the above-described procedure until defect detections for all of the inspection areas are finished.

As described above, according to the present embodiment, the degree of the gradient of the edge profile is checked before a pattern inspection. Depending on whether the gradient is steep or gentle, the first or second inspection technique based on the outer shape comparison or the third inspection technique based on the pixel value comparison is selected. Thus, the inspection speed can be improved when, for example, sufficient edge contrast cannot be expected in an inspection pattern image to be acquired.

(C) Program

Figure 2:
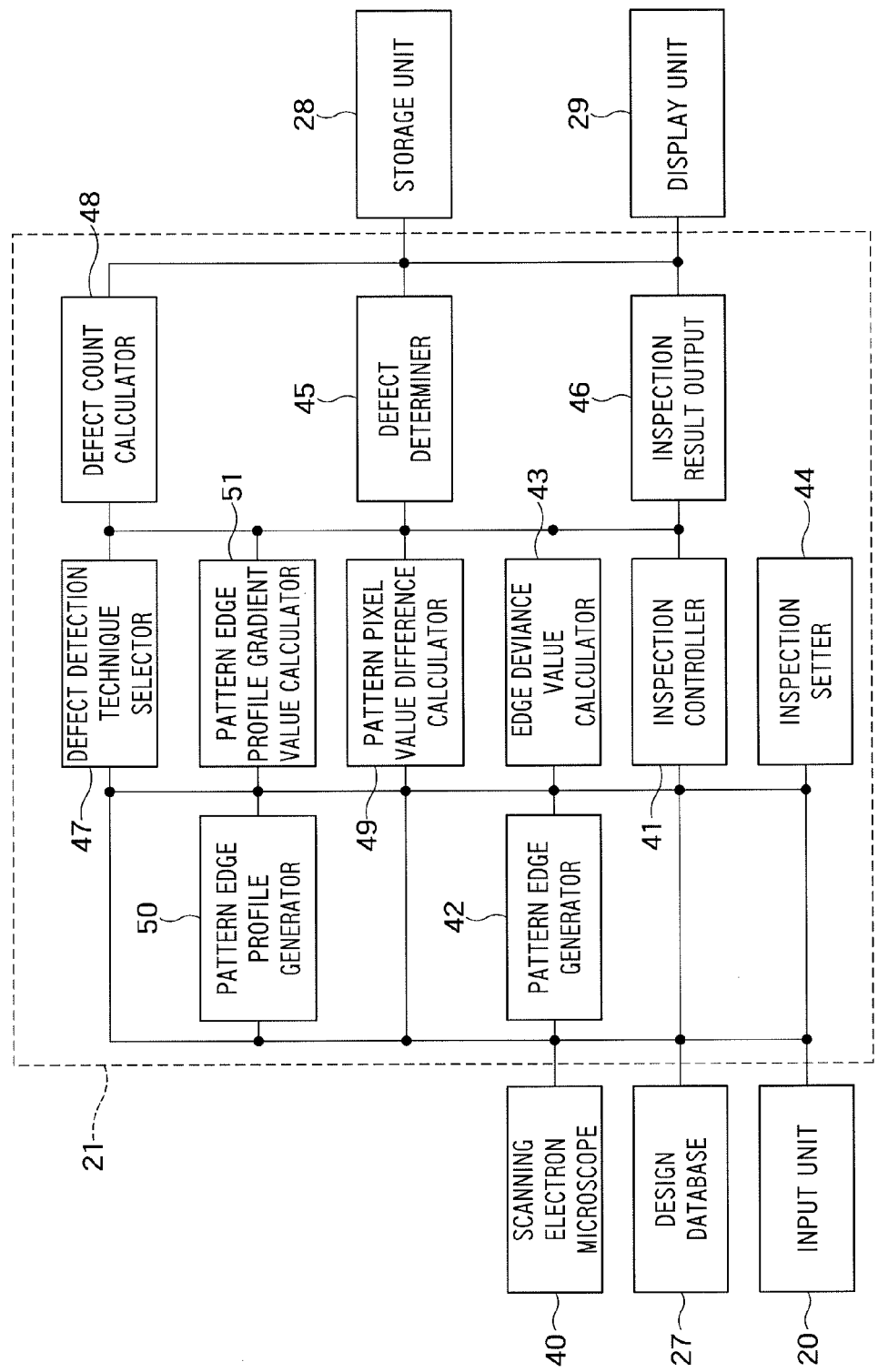
FIG. 2 is a block diagram showing a detailed configuration of a control computer of the pattern inspection apparatus shown in FIG. 1.

While the pattern inspection method using the pattern inspection apparatus shown in FIG. 1 and FIG. 2 has been described in the above embodiments, the series of inspection process described above may be incorporated in a program as a recipe file, and read into and executed by a general-purpose computer such as an EWS capable of processing an SEM image. This enables the pattern inspection method according to the first to third embodiments described above to be carried out by use of the general-purpose computer.

In this case, the pattern inspection apparatus comprising the control computer 21 shown in FIG. 1 and FIG. 2 is not exclusively used. For example, if the second inspection technique is used instead of the first inspection technique in the process of step S71 in FIG. 13, the pattern inspection method according to the third embodiment described above can be carried out by use of a computer incapable of loading design data.

Moreover, the series of processes of the pattern inspection method described above may be incorporated in a program to be executed by a computer as a processing procedure, and this program may be stored in a recording medium such as a flexible disk or a CD-ROM and read into and executed by a computer. The recording medium is not limited to a portable medium such as a magnetic disk or an optical disk, and may be a fixed recording medium such as a hard disk drive or a memory.

(D) Semiconductor Device Manufacturing Method

A semiconductor device can be manufactured with high throughput and yield by a process that includes a high-speed and low-load inspection process using the pattern inspection method described above.

More specifically, a substrate is extracted per production lot, and a pattern formed on the extracted substrate is inspected by the pattern inspection method described above. When the substrate is judged as a nondefective product as a result of the inspection, the rest of the manufacturing process is continuously executed for the whole production lot to which the inspected substrate belongs. On the other hand, when the substrate is judged as a defective product as a result of the inspection and can be reworked, the production lot to which the substrate judged as the defective product belongs is reworked. When the rework is finished, the substrate is extracted from the production lot and again inspected. If the extracted substrate is judged as a nondefective product as a result of the reinspection, the rest of the manufacturing process is executed for the reworked production lot. When the rework processing is impossible, the production lot to which the substrate judged as the defective product belongs is disposed of. The cause of the defect is analyzed, and results of the analysis are fed back to a person in charge of designing, a person in charge of an upstream process or the like.

(E) Addition

According to the embodiments described above, it is possible to reduce false defects and output an inspection result at high speed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A pattern inspection method comprising:
imaging a first pattern formed in a first area of a substrate to acquire a first pattern image;
associating the first pattern image with design information for the first pattern to detect a defect by a die-to-database inspection;
comparing the number of the detected defect with a prepared first threshold, and when the number of the detected defects is equal to or less than the first threshold, outputting the detected defect as an inspection result;
imaging a second pattern to acquire a second pattern image when the number of the detected defect is more than the first threshold, the second pattern being formed in a second area different from the first area within the substrate and being designed to comprise the same shape as the first pattern; and
comparing the first pattern image with the second pattern image to further detect a defect by a die-to-die inspection, and outputting the further detected defects as an inspection result,
wherein the further detection of defect by the die-to-die inspection comprises:
detecting an edge of the first pattern from the first pattern image, and calculating a value of a gradient of a detected edge profile of the first pattern;
comparing the value of the gradient with a prepared second threshold; and
detecting an edge of the second pattern from the second pattern image and comparing the edge of the second pattern with the edge of the first pattern to detect a defect when the calculated value of the gradient is equal to or more than the second threshold, or calculating a pixel value of the first pattern image and a pixel value of the second pattern image and comparing these pixel values to detect a defect when the calculated value of the gradient is less than the second threshold.

2. A pattern inspection method comprising:
imaging a first pattern formed in a first area of a substrate to acquire a first image;
detecting an edge of the first pattern from the first image, and calculating a gradient of a detected edge profile of the first pattern;
comparing the gradient with a prepared first threshold; and
detecting a defect by an outer shape comparison using at least one of a die-to-database inspection and a die-to-die inspection when the calculated value of the gradient is equal to or more than the first threshold, or imaging a second pattern to acquire a second image and comparing pixel values of the first image and the second image to detect a defect when the calculated value of the gradient is less than the first threshold, the second pattern being formed in a second area different from the first area within the substrate and being designed to comprise the same shape as the first pattern.

3. The method of claim 2, wherein the defect detection by the outer shape comparison comprises:
comparing the number of the defect detected by the die-to-database inspection with a prepared second threshold, and when the number of the detected defect is equal to or less than the second threshold, outputting the detected defect as an inspection result, or when the number of the detected defect is more than the second threshold, imaging the second pattern to acquire a second image, further detecting a defect by the die-to-die inspection based on a comparison between the first image and the second image, and outputting the further detected defect as an inspection result.

4. The method of claim 2, further comprising, in the defect detection by the outer shape comparison, selecting the die-to-database inspection or the die-to-die inspection depending on whether a database in an inspection apparatus is available.

5. The method of claim 2, wherein the first threshold is set for each of inspection areas obtained by dividing the entire area of the substrate.

6. The method of claim 2, wherein the patterns to be inspected comprise a plurality of kinds of patterns; and
the first threshold is set for each kind of pattern.

* * * * *